(12) United States Patent
Choi et al.

(10) Patent No.: US 11,466,239 B2
(45) Date of Patent: Oct. 11, 2022

(54) BIOLOGICAL MATERIAL MANUFACTURING DEVICE AND DRIVING METHOD THEREOF

(71) Applicant: VIEA LOGIS Co., Ltd., Seoul (KR)

(72) Inventors: Chul-Hong Choi, Seoul (KR); Dong-Wook Shin, Seongnam-si (KR); In-Sang Yoon, Seoul (KR); Jung-Min Kim, Seoul (KR)

(73) Assignee: VIEA Logis Co., Ltd., Seoul (KR)

( * ) Notice: Subject to any disclaimer, the term of this patent is extended or adjusted under 35 U.S.C. 154(b) by 357 days.

(21) Appl. No.: 16/779,266

(22) Filed: Jan. 31, 2020

(65) Prior Publication Data

US 2020/0248117 A1 Aug. 6, 2020

(30) Foreign Application Priority Data

Feb. 1, 2019 (KR) .......................... 10-2019-0013260

(51) Int. Cl.
*C12M 3/00* (2006.01)
*B01L 3/00* (2006.01)
*B01L 7/00* (2006.01)

(52) U.S. Cl.
CPC .............. *C12M 21/08* (2013.01); *B01L 3/527* (2013.01); *B01L 7/00* (2013.01); *B01L 2200/16* (2013.01); *B01L 2300/0832* (2013.01); *B01L 2300/1805* (2013.01)

(58) Field of Classification Search
None
See application file for complete search history.

(56) References Cited

U.S. PATENT DOCUMENTS

| 2012/0160714 A1* | 6/2012 | Nozaki ................ C12M 21/08 206/205 |
| 2012/0316050 A1* | 12/2012 | Daub ..................... B01F 29/321 494/37 |
| 2019/0046972 A1* | 2/2019 | Mulakkapurath Narayanan ......... G01N 1/34 |

FOREIGN PATENT DOCUMENTS

| JP | 6-79678 B2 | 10/1994 |
| JP | 2011-147924 A | 8/2011 |
| JP | 2012-166178 A | 9/2012 |
| KR | 10-1696107 B1 | 1/2017 |

* cited by examiner

*Primary Examiner* — Matthew D Krcha
(74) *Attorney, Agent, or Firm* — Lewis Reca Rethgerber Christie LLP

(57) ABSTRACT

A biological material manufacturing device according to an embodiment of the inventive concept includes a main body and a head unit that is rotatable on the main body. The main body includes a main groove and a first container groove connected to the main groove. The head unit includes a pillar provided in the main groove and a protruding part that protrudes from the pillar.

9 Claims, 16 Drawing Sheets

BIOLOGICAL MATERIAL MANUFACTURING DEVICE AND DRIVING METHOD THEREOF

CROSS-REFERENCE TO RELATED APPLICATIONS

This U.S. non-provisional patent application claims priority under 35 U.S.C. § 119 of Korean Patent Application No. 10-2019-0013260, filed on Feb. 1, 2019, the entire contents of which are hereby incorporated by reference.

BACKGROUND

The present disclosure herein relates to a biological material manufacturing device and a driving method thereof. Particularly, the present disclosure relates to a biological material manufacturing device that manufactures a biological material by using a body tissue of a human or an animal and a driving method thereof. More particularly, the present disclosure relates to a biological material manufacturing device that manufactures a biological material by using a hair, a nail, or a toenail of a human and a driving method thereof.

A product manufactured by using a biological material that is manufactured by using a body tissue of a human or an animal may be used for various purposes. Lovers may feel mutual presence by possessing a product manufactured by using their body tissues, a fan may feel a close identity with a favorite celebrity by possessing a product manufactured by using a body tissue of the celebrity, and a person may possess a product manufactured by using a body tissue in order to eternally remember a person or a pet.

SUMMARY

The present disclosure provides a biological material manufacturing device capable of manufacturing a biological material using a human hair in a simple and safe manner.

An embodiment of the inventive concept provides a biological material manufacturing device including: a main body; and a head unit that is rotatable on the main body. Here, the main body includes a main groove and a first container groove connected to the main groove, the head unit includes a pillar provided in the main groove and a protruding part that protrudes from the pillar.

In an embodiment, a first container, in which a first solution is accommodated, may be provided in the first container groove, the first solution may be an acidic solution, and the protruding part may contact the first container according to rotation of the head unit.

In an embodiment, the main body may further include a second container groove connected to the main groove, a second container, in which a second solution is accommodated, may be provided in the second container groove, and the second solution may react with the first solution to neutralize the first solution.

In an embodiment, the main body may further include an insertion groove connected to the main groove, each of a bottom surface of the main groove and a bottom surface of the insertion groove may be inclined to a top surface of the main body, and the bottom surface of the insertion groove may have a level less than that of the bottom surface of the main groove.

In an embodiment, the main body may further include a heater disposed below the insertion groove.

In an embodiment, the main body may further include a neutralizer groove connected to the main groove, a first neutralizer supported by the pillar may be provided in the neutralizer groove, the pillar may include a recess at a side surface thereof, and the first neutralizer may enter into the recess according to the rotation of the head unit to neutralize the first solution.

In an embodiment, the main body may further include a discharge groove connected to the main groove, the discharge groove may include a discharge surface that is inclined to a top surface of the main body, the discharge groove may further include a second neutralizer disposed on the discharge surface, and the second neutralizer may neutralize the first solution.

In an embodiment of the inventive concept, a method for driving a biological material manufacturing device includes: inserting a body tissue into a main body; dissolving the body tissue in a first solution; and neutralizing the first solution. Here, the dissolving of the body tissue in the first solution includes: disposing a first container, in which the first solution is accommodated, in a first container groove of the main body; rotating a head unit disposed on the main body; and cutting or crushing the first container by a protruding part of the head unit.

In an embodiment, the neutralizing of the first solution may include: disposing a second container, in which a second solution is accommodated, in a second container groove of the main body; rotating the head unit; and cutting or crushing the second container by the protruding part of the head unit.

In an embodiment, the neutralizing of the first solution may include: producing a biological material that is primarily neutralized by mixing the first solution with a second solution; secondarily neutralizing the primarily neutralized biological material by being reacted with a first neutralizer; and tertiarily neutralizing the secondarily neutralized biological material by being reacted with a second neutralizer.

BRIEF DESCRIPTION OF THE FIGURES

The accompanying drawings are included to provide a further understanding of the inventive concept, and are incorporated in and constitute a part of this specification. The drawings illustrate exemplary embodiments of the inventive concept and, together with the description, serve to explain principles of the inventive concept. In the drawings.

DETAILED DESCRIPTION

Figure 1:
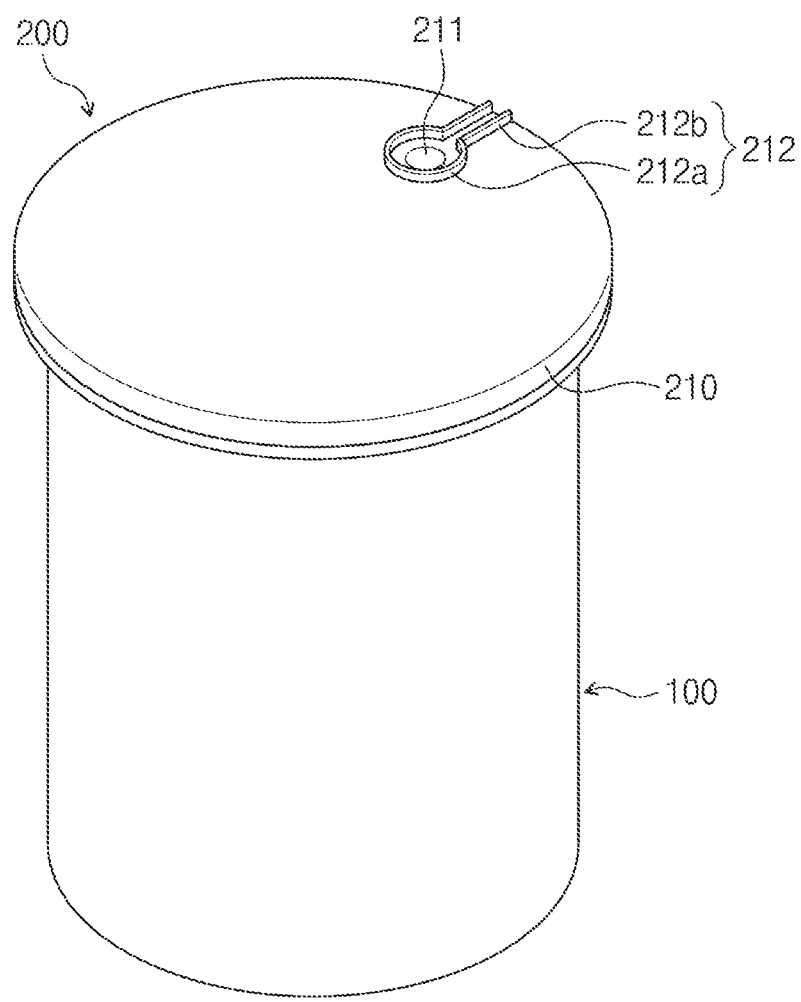
FIG. 1 is a perspective view illustrating a biological material manufacturing device according to an embodiment of the inventive concept.

Advantages and features of the present invention, and implementation methods thereof will be clarified through following embodiments described with reference to the accompanying drawings. The present invention may, however, be embodied in many different forms and should not be construed as being limited to the embodiments set forth herein. Rather, these embodiments are provided so that this disclosure will be thorough and complete, and will fully convey the concept of the invention to those skilled in the art. Further, the present invention is only defined by scopes of claims. Like reference numerals refer to like elements throughout.

In the following description, the technical terms are used only for explaining a specific exemplary embodiment while not limiting the present disclosure. The terms of a singular form may include plural forms unless referred to the contrary. The meaning of "include," "comprise," "including," or "comprising," specifies a property, a region, a fixed number, a step, a process, an element and/or a component but does not exclude other properties, regions, fixed numbers, steps, processes, elements and/or components. Hereinafter, embodiments of the inventive concept will be described in detail.

Figure 2:
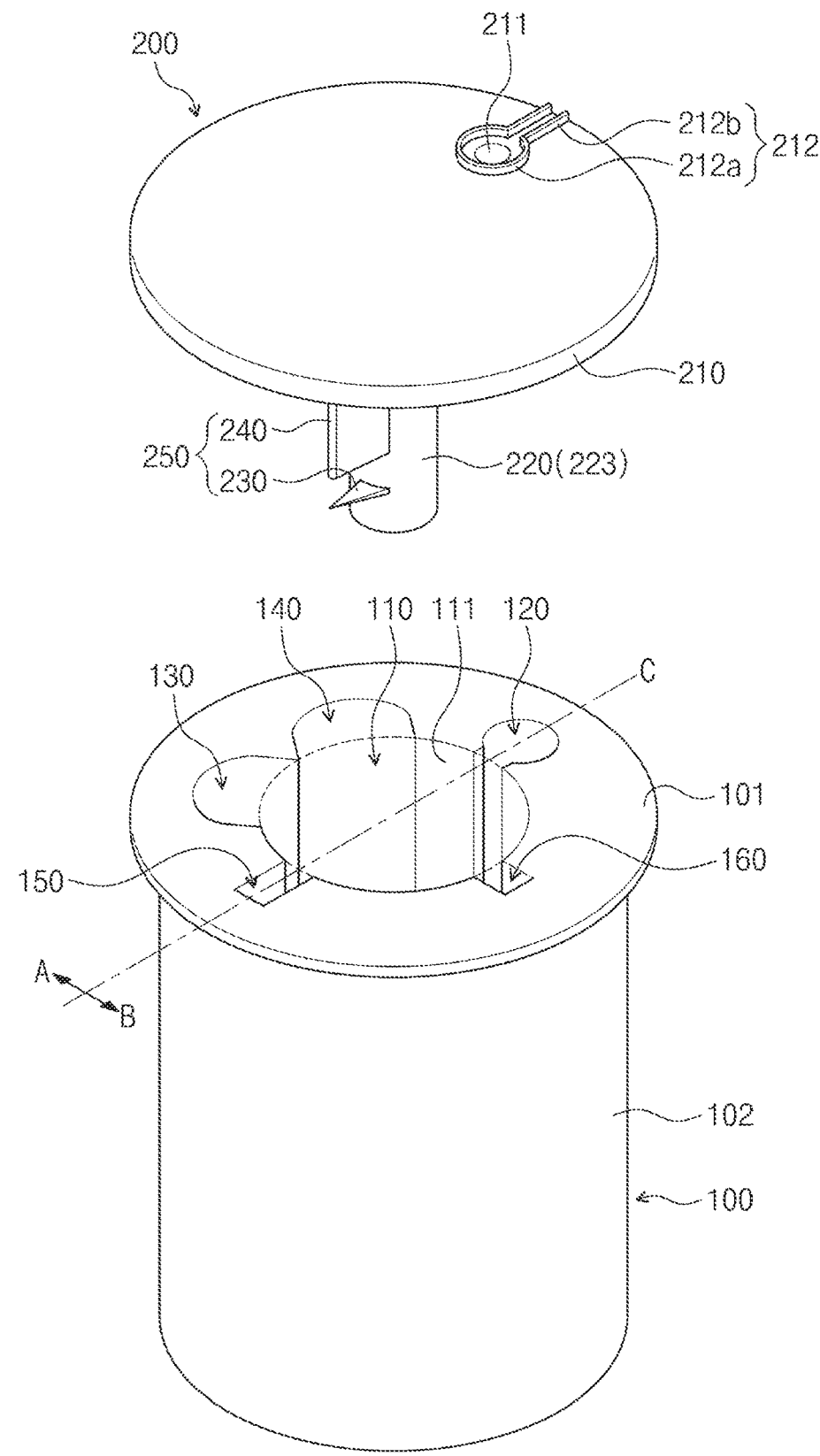
FIG. 2 is an exploded perspective view illustrating the biological material manufacturing device according to an embodiment of the inventive concept.
Figure 3:
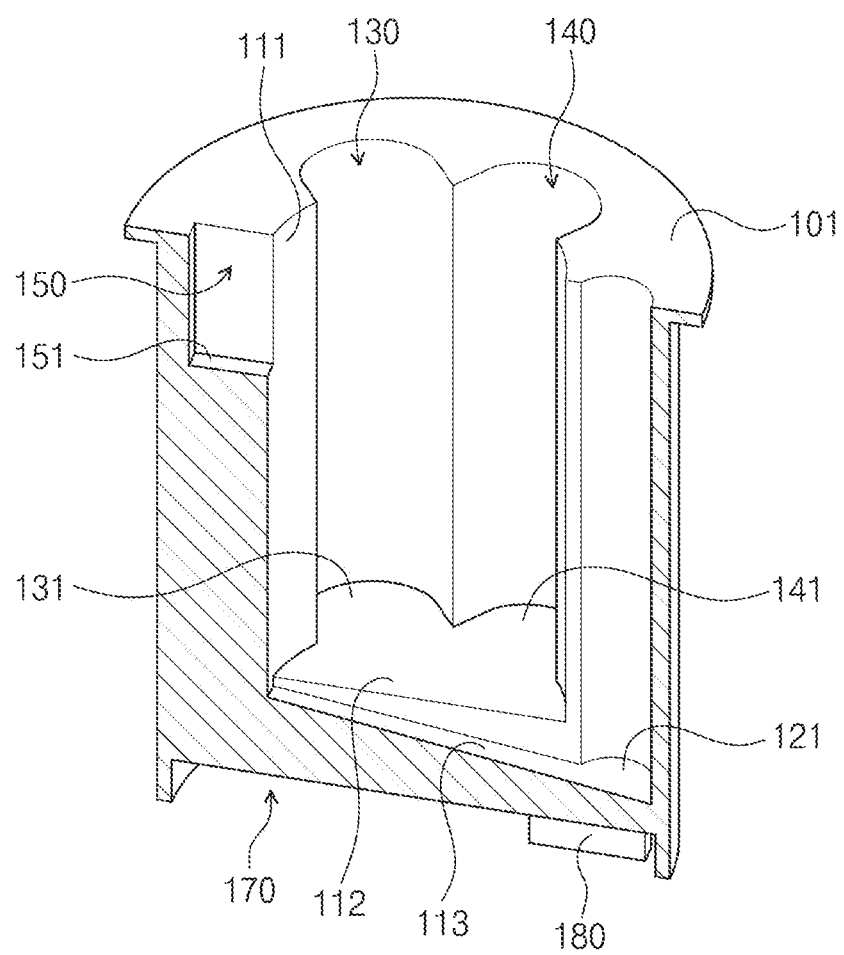
FIG. 3 is a cross-sectional perspective view taken along line C in a direction A of FIG. 2.
Figure 4:
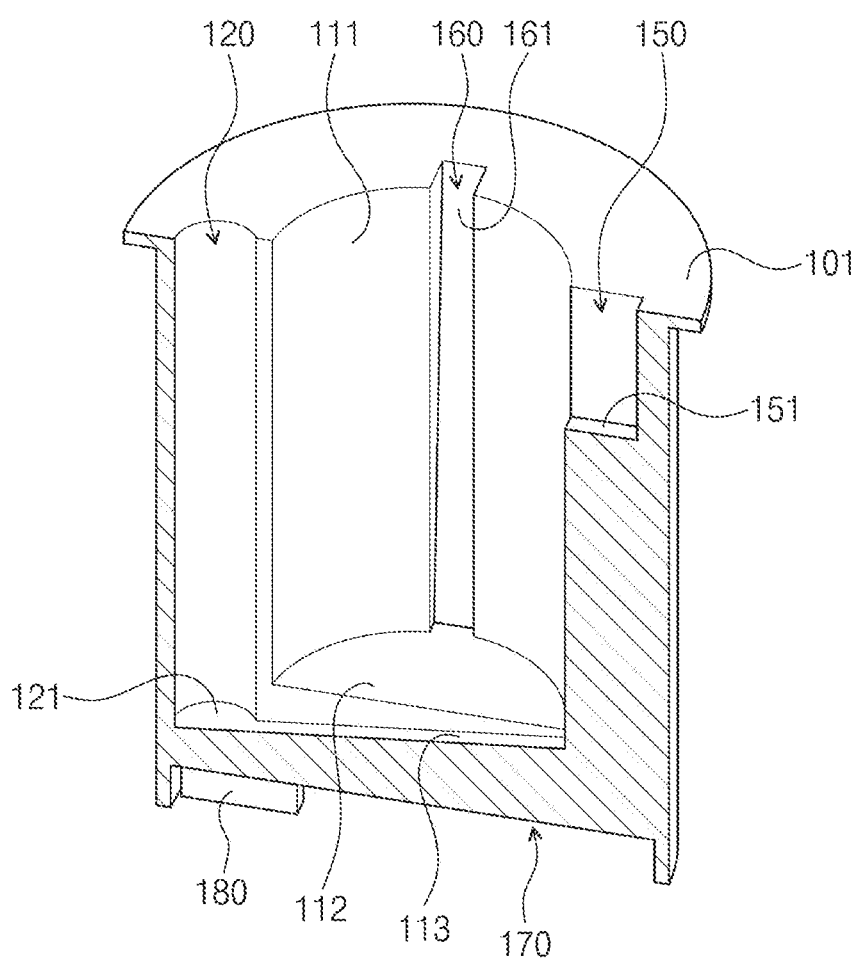
FIG. 4 is a cross-sectional perspective view taken along line C in a direction B of FIG. 2.
Figure 5:
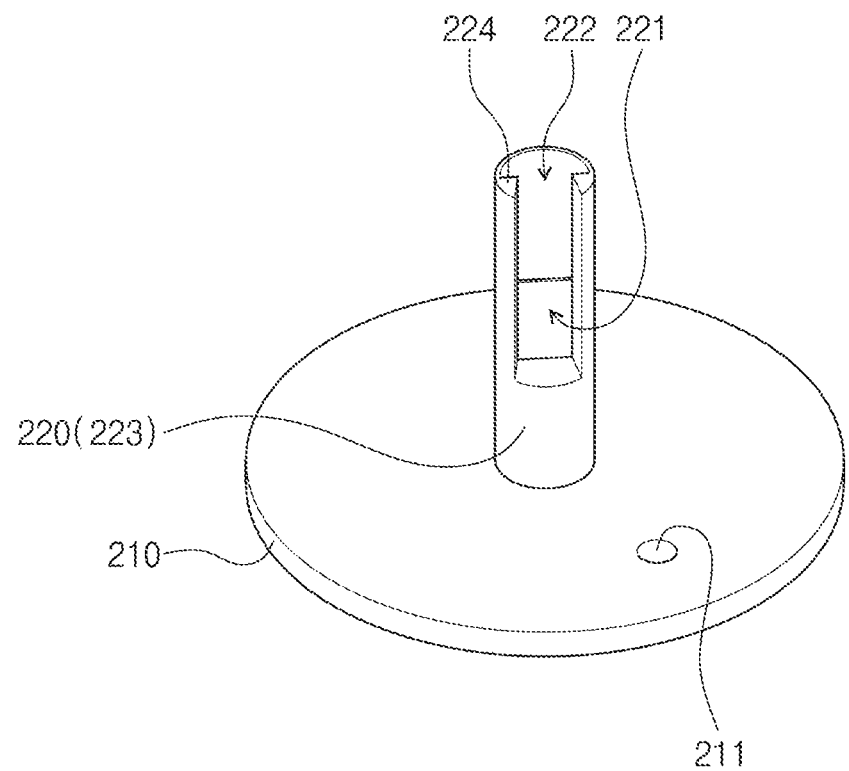
FIG. 5 is a perspective view for explaining a head unit.

FIG. 1 is a perspective view illustrating a biological material manufacturing device according to an embodiment of the inventive concept. FIG. 2 is an exploded perspective view illustrating the biological material manufacturing device according to an embodiment of the inventive concept. FIG. 3 is a cross-sectional perspective view taken along line C in a direction A of FIG. 2. FIG. 4 is a cross-sectional perspective view taken along line C in a direction B of FIG. 2. FIG. 5 is a perspective view for explaining a head unit.

Referring to FIGS. 1, 2, 3, 4, and 5, the biological material manufacturing device according to an embodiment of the inventive concept may include a main body 100 and a head unit 200.

The main body 100 may have a cylindrical shape. The main body 100 may include a main groove 110, an insertion groove 120, a first container groove 130, a second container groove 140, a neutralizer groove 150, and a discharge groove 160. As a portion of a top surface 101 of the main body 100 is recessed, the main groove 110, the insertion groove 120, the first container groove 130, the second container groove 140, the neutralizer groove 150, and the discharge groove 160 may be provided. The insertion groove 120, the first container groove 130, the second container groove 140, the neutralizer groove 150, and the discharge groove 160 may be connected to the main groove 110. In terms of a plane, the circular main groove 110 may be defined at a center of the main body 100, and the insertion groove 120, the first container groove 130, the second container groove 140, the neutralizer groove 150, and the discharge groove 160 may be connected to an outside of the main groove 110. The insertion groove 120, the first container groove 130, the second container groove 140, the neutralizer groove 150, and the discharge groove 160 may be defined as a side surface 111 of the main groove 110 is recessed in a direction toward an outer wall 102 of the main body 100. The insertion groove 120, the first container groove 130, the second container groove 140, the neutralizer groove 150, and the discharge groove 160 may be spaced apart from each other with the main groove 110 therebetween. In terms of the plane, the insertion groove 120 and the neutralizer groove 150 may be disposed on a straight line. The first and second container grooves 130 and 140 may be disposed between the insertion groove 120 and the neutralizer groove 150. The discharge groove 160 may be disposed between the insertion groove 120 and the neutralizer groove 150.

The main groove 110 may include first bottom surfaces 112 and a second bottom surface 113 disposed between the first bottom surfaces 112. In terms of the plane, the second bottom surface 113 of the main groove 110 may be provided along a straight line connecting the insertion groove 120 and the neutralizer groove 150.

The first bottom surfaces 112 of the main groove 110 may be parallel to the top surface 101 of the main body 100. The first bottom surfaces 112 of the main groove 110 may provide a coplanar surface with a bottom surface 131 of the first container groove 130 and a bottom surface 141 of the second container groove 140. In other words, the first bottom surfaces 112 of the main groove 110, the bottom surface 131 of the first container groove 130, and the bottom surface 141 of the second container groove 140 may be provided at the same level. The level may represent a minimum distance from a bottom of the main body 100. As the level decreases, the minimum distance from the bottom of the main body 100 decreases.

The second bottom surface 113 of the main groove 110 may have a level less than that of the first bottom surface 112. The second bottom surface 113 of the main groove 110 may be inclined to the top surface 101 of the main body 100. The second bottom surface 113 of the main groove 110 may have a level that gradually decreases in a direction toward the insertion groove 120.

The bottom surface 121 of the insertion groove 120 may be inclined to the top surface 101 of the main body 100. The bottom surface 121 of the insertion groove 120 may provide a coplanar surface with the second bottom surface 113 of the main groove 110. The bottom surface 121 of the insertion groove 120 may have a level that gradually increases in a direction toward the main groove 110. The bottom surface 121 of the insertion groove 120 may have an average level less than that of the second bottom surface 113 of the main groove 110.

A bottom surface 151 of the neutralizer groove 150 may have a level greater than that of the first bottom surface 112 of the main groove 110. In other words, the neutralizer groove 150 may be positioned at a relatively higher level than the main groove 110.

A discharge surface 161 of the discharge groove 160 may be inclined to the top surface 101 of the main body 100. The discharge surface 161 of the discharge groove 160 may be gradually close to the outer wall 102 of the main body 100 in a direction from a lower portion to an upper portion.

The main body 100 may further include a lower groove 170 and a heater 180. The lower groove 170 may be defined as the bottom of the main body 100 is recessed in a direction toward the top surface 101 of the main body 100. The heater 180 may be disposed in the lower groove 170. The heater 180 may be disposed below the insertion groove 120. In other words, the heater 180 may perpendicularly overlap the insertion groove 120.

The head unit 200 may include a base 210, a pillar 220, and a protruding part 250.

The base 210 may have a circular plate shape. The base 210 may be disposed on the top surface 101 of the main body 100. The base 210 may rotate clockwise or counter-clockwise on the top surface 101 of the main body 100.

The base 210 may include a base opening 211 and a barrier 212. The base opening 211 may pass through the base 210. The inside of the main body 100 and a space above the base 210 may communicate by the base opening 211.

The barrier 212 may protrude from a top surface of the base 210. The barrier 212 may include a first portion 212a and second portions 212b. The first portion 212a has a C-shape on a plane. In terms of the plane, the base opening 211 is defined in the first portion 212a.

The second portions 212b of the barrier 212 may be connected to the first portion 212a. Each of the second portions 212b may have a bar shape. The second portions 212b may extend in parallel to each other. The second portions 212b may extend from the first portion 212a to an edge of the top surface of the base 210.

The pillar 220 may have a cylindrical shape. The pillar 220 may extend downward from the base 210. The pillar 220 may be disposed in the main groove 110 of the main body 100. The pillar 220 may include a first recess 221 and a second recess 222. The first recess 221 and the second recess 222 may be defined as a side surface 223 of the pillar 220 is recessed. The first and second recesses 221 and 222 may vertically overlap each other. The first recess 221 may have a recessed depth greater than that of the second recess 222. In other words, the second recess 222 may be recessed deeper than the first recess 221. The second recess 222 may be disposed at a lower portion of the pillar 220. The first recess 221 may be disposed above the second recess 222.

The side surface 223 of the pillar 220 may be spaced apart from the side surface 111 of the main groove 110 of the main body 100. A bottom surface 224 of the pillar 220 may be spaced apart from the first and second bottom surfaces 112 and 113 of the main groove 110 of the main body 100.

The protruding part 250 may include a cutting portion 230 and a pressing portion 240. One portion of the protruding part 250 may be the cutting portion 230, and the other portion of the protruding part 250 may be the pressing portion 240.

The cutting portion 230 may protrude from the side surface 223 of the pillar 220. The cutting portion 230 may have a relatively small thickness. Here, a thickness direction of the cutting portion 230 may be parallel to an axial direction (i.e., an axial direction of the cylinder) of the pillar 220. The cutting portion 230 may include a sharp portion. For example, the cutting portion 230 may have a blade shape. A blade direction of the cutting portion 230 may be perpendicular to the axial direction of the pillar 220. The cutting portion 230 may protrude from the side surface 223 of the pillar 220 to the side surface 111 of the main groove 110. In terms of the plane, the cutting portion 230 may have a maximum length that is less than a minimum distance between the side surface 223 of the pillar 220 and the side surface 111 of the main groove 110. Thus, the cutting portion 230 may be spaced apart from the side surface 111 of the main groove 110.

The pressing portion 240 may protrude from the side surface 223 of the pillar 220. The pressing portion 240 may be disposed above the cutting portion 230. The pressing portion 240 may perpendicularly overlap the cutting portion 230. The cutting portion 240 may have a relatively large thickness. The pressing portion 240 may have a thickness greater than that of the cutting portion 230. Here, a thickness direction of the pressing portion 240 may be parallel to the axial direction of the pillar 220. The pressing portion 240 may protrude from the side surface 223 of the pillar 220 to the side surface 111 of the main groove 110. In terms of the plane, the pressing portion 240 may have a maximum length that is less than the minimum distance between the side surface 223 of the pillar 220 and the side surface 111 of the main groove 110. Thus, the pressing portion 240 may be spaced apart from the side surface 111 of the main groove 110.

Each of the pillar 220, the cutting portion 230, and the pressing portion 240 may rotate clockwise or counter-clockwise according to rotation of the base 210.

FIGS. 6, 7A, 8A, 9A, 10A, and 11A are views for explaining a method for driving the biological material manufacturing device according to an embodiment of the inventive concept. FIG. 7B is a cross-sectional view taken along line I-I' of FIG. 7A. FIG. 8B is a cross-sectional view taken along line II-II' of FIG. 8A. FIG. 9B is a cross-sectional view taken along line III-III' of FIG. 9A. FIG. 10B is a cross-sectional view taken along line IV-IV' of FIG. 10A. FIG. 11B is a cross-sectional view taken along line V-V' of FIG. 11A.

Figure 6:
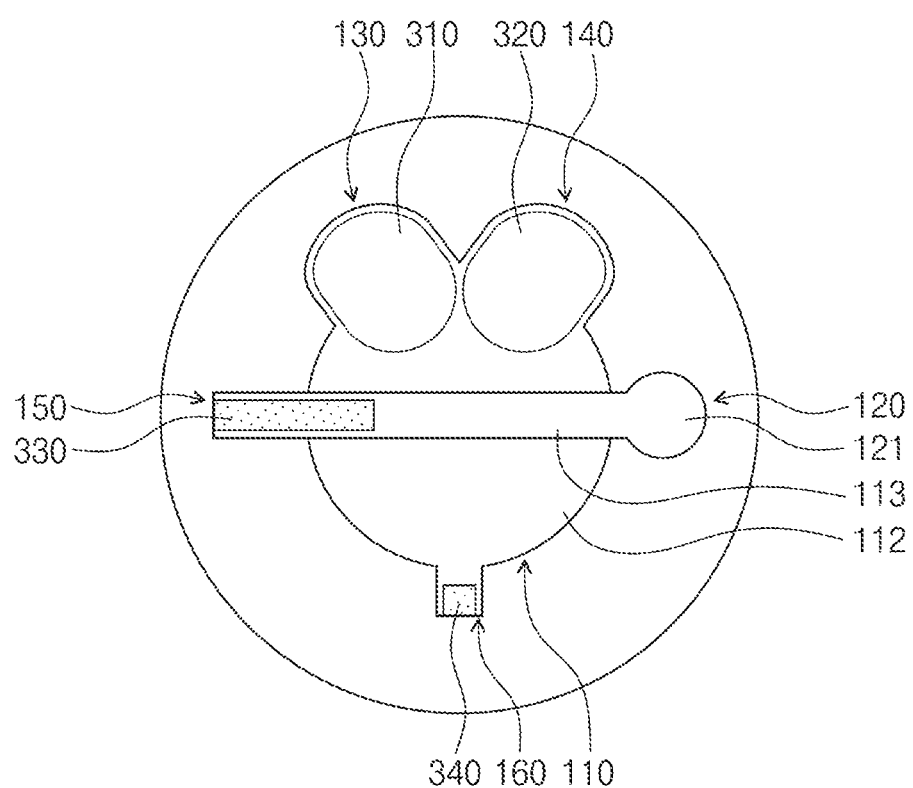
FIGS. 6, 7A, 8A, 9A, 10A, and 11A are views for explaining a method for driving the biological material manufacturing device according to an embodiment of the inventive concept.

Referring to FIG. 6, a first container 310 may be disposed in the first container groove 130 of the main body 100. The first container 310 may be disposed in the first container groove 130 and a portion of the main groove 110, which is connected to the first container groove 130. The first container 310 may be disposed so that a minimum distance between the first container 310 and the pillar 220 is less than that between the side surface 111 of the main groove 110 and the pillar 220. The first container 310 may accommodate a first solution 311 (refer to FIG. 8B). The first solution 311 may include a material capable of dissolving a body tissue BT (refer to FIG. 7B) that will be described later. The first solution 311 may be acidic. For example, the first solution 311 may be a nitric acid ($HNO_3$) solution, a hydrochloric acid (HCl) solution, or a sulfuric acid ($H_2SO_4$) solution. The first container 310 may be made of a material that is cut by a sharp object such as a blade. For example, the material of the first container 310 may be a resin containing a polymer. For another example, the material of the first container 310 may be glass.

A second container 320 may be disposed in the second container groove 140 of the main body 100. The second container 320 may be disposed in the second container groove 140 and a portion of the main groove 110, which is connected to the second container groove 140. The second container 320 may be disposed so that a minimum distance between the second container 320 and the pillar 220 is less than that between the side surface 111 of the main groove 110 and the pillar 220. The second container 320 may accommodate a second solution 321 (refer to FIG. 9B). The second solution 321 and the first solution 311 may react with each other to increase an acidity (pH) of the first solution 311. In other words, an acidity (pH) of a material obtained by mixing the first solution 311 and the second solution 321 may be greater than that of the first solution 311. In other words, the second solution 321 may neutralize the first solution 311. Neutralization caused by the second solution 321 may be defined as primary neutralization. For example, the second solution 321 may be a calcium carbonate ($CaCO_3$) solution.

The first solution 311 and the second solution 321 may be reacted according to a chemical equation 1, a chemical equation 2, or a chemical equation 3

$$2HNO_3 + CaCO_3 \rightarrow Ca(NO_3)_2 + CO_2 + H_2O \quad \text{(chemical equation 1)}$$

$$2HCL + CaCO_3 \rightarrow CaCl_2 + CO_2 + H_2O \quad \text{(chemical equation 2)}$$

$$H_2SO_4 + CaCO_3 \rightarrow CaSO_4 + CO_2 + H_2O \quad \text{(chemical equation 3)}$$

The second container 320 may be made of a material capable of being cut by a sharp object such as a blade. For example, the material of the second container 320 may be a resin containing a polymer. For another example, the material of the second container 320 may be glass.

A first neutralizer 330 may be disposed in the neutralizer groove 150 of the main body 100. The first neutralizer 330 may have a cylindrical shape. The first neutralizer 330 may be disposed so that a circumferential surface (i.e., a side surface of the cylinder) thereof contacts the bottom surface 151 of the neutralizer groove 150. The first neutralizer 330 may react with the first solution 311 (or a material produced by mixing the first solution 311 and the second solution 321) to increase the acidity (pH) of the first solution 311 (or the material produced by mixing the first solution 311 and the second solution 321). In other words, the first neutralizer 330 may neutralize the first solution 311 (or the material produced by mixing the first solution 311 and the second solution 321). Neutralization caused by the first solution 330 may be defined as secondary neutralization. For example, the first solution 330 may contain a calcium carbonate ($CaCO_3$) solution.

A second neutralizer 340 may be disposed on the discharge surface 161 of the discharge groove 160. The second neutralizer 340 may react with the first solution 311 (or the material produced by mixing the first solution 311 and the second solution 321) to increase the acidity (pH) of the first solution 311 (or the material produced by mixing the first solution 311 and the second solution 321). In other words, the second neutralizer 340 may neutralize the first solution 311 (or the material produced by mixing the first solution 311 and the second solution 321). Neutralization caused by the second solution 340 may be defined as tertiary neutralization. For example, the second solution 340 may contain a calcium carbonate ($CaCO_3$) solution.

After the first container 310, the second container 320, the first neutralizer 330, and the second neutralizer 340 are disposed, the main body 100 may be covered by the head unit 200. The head unit 200 and the main body 100 may be coupled so that the base opening 211 of the base 210 perpendicularly overlaps the insertion groove 120 of the main body 100. As the first neutralizer 330 is supported by the pillar 220 of the head unit 200, the first neutralizer 330 may not be fallen from the neutralizer groove 150 to the second bottom surface 113 of the main groove 110. The pillar 220 may support the first neutralizer 330 at one side thereof.

Figure 7A:
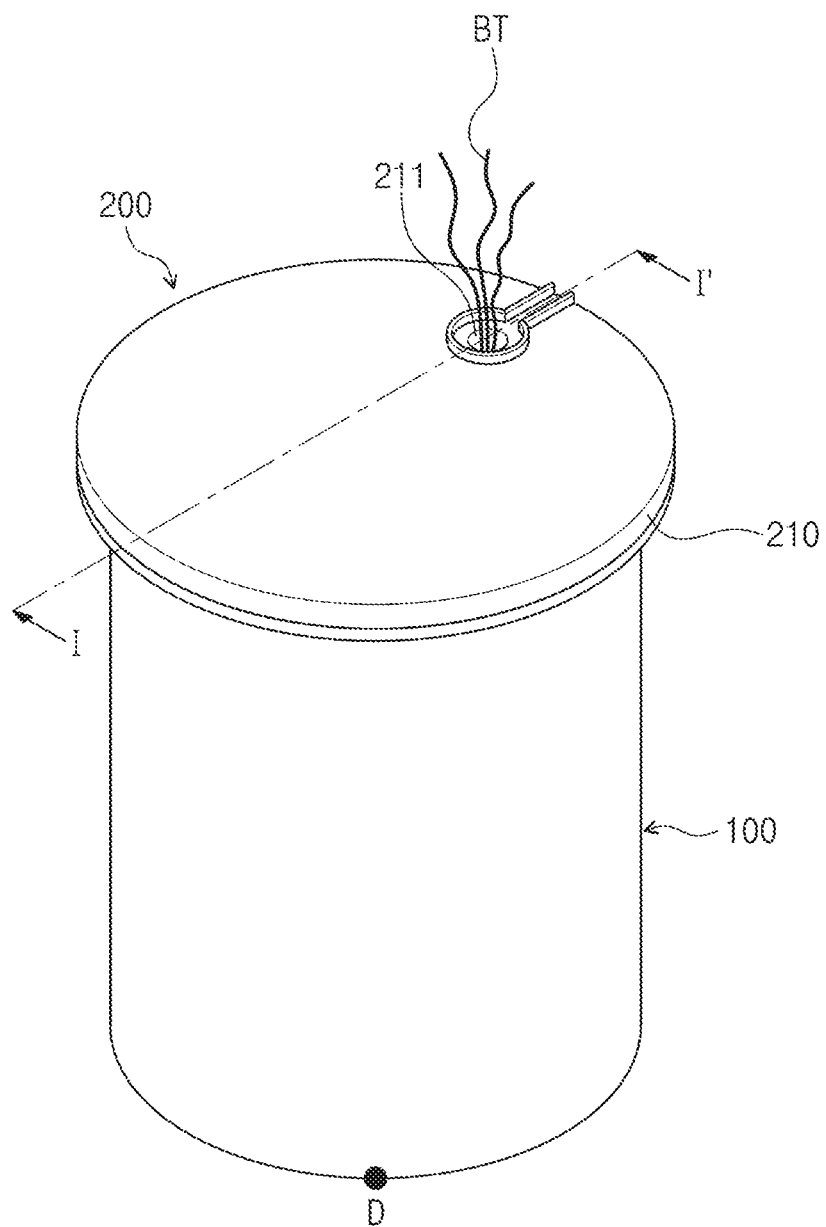
Figure 7B:
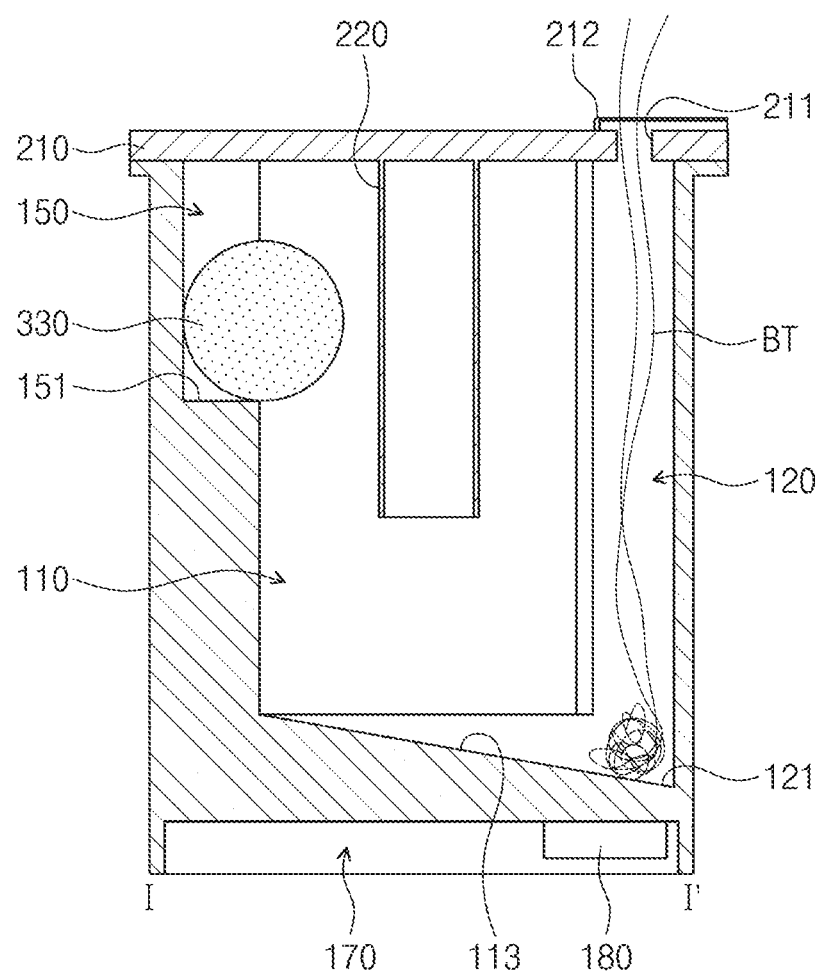
FIG. 7B is a cross-sectional view taken along line I-I' of FIG. 7A.

Referring to FIGS. 7A and 7B, the body tissue BT may be inserted through the base opening 211 of the base 210. The body tissue BT may be a body tissue of a human or an animal. For example, the body tissue BT may be a human hair. For another example, the body tissue BT may be a nail or a toenail of a human.

The body tissue BT may be injected into the injection groove 120 of the main body 100 through the base opening 211. A bar-type tool may be used to smoothly insert the body tissue BT. For example, as a portion of the body tissue BT is inserted into the base opening 211, and then another portion of the body tissue BT is pushed down by using the tool, the entire body tissue BT may be inserted into the insertion groove 120.

Figure 8A:
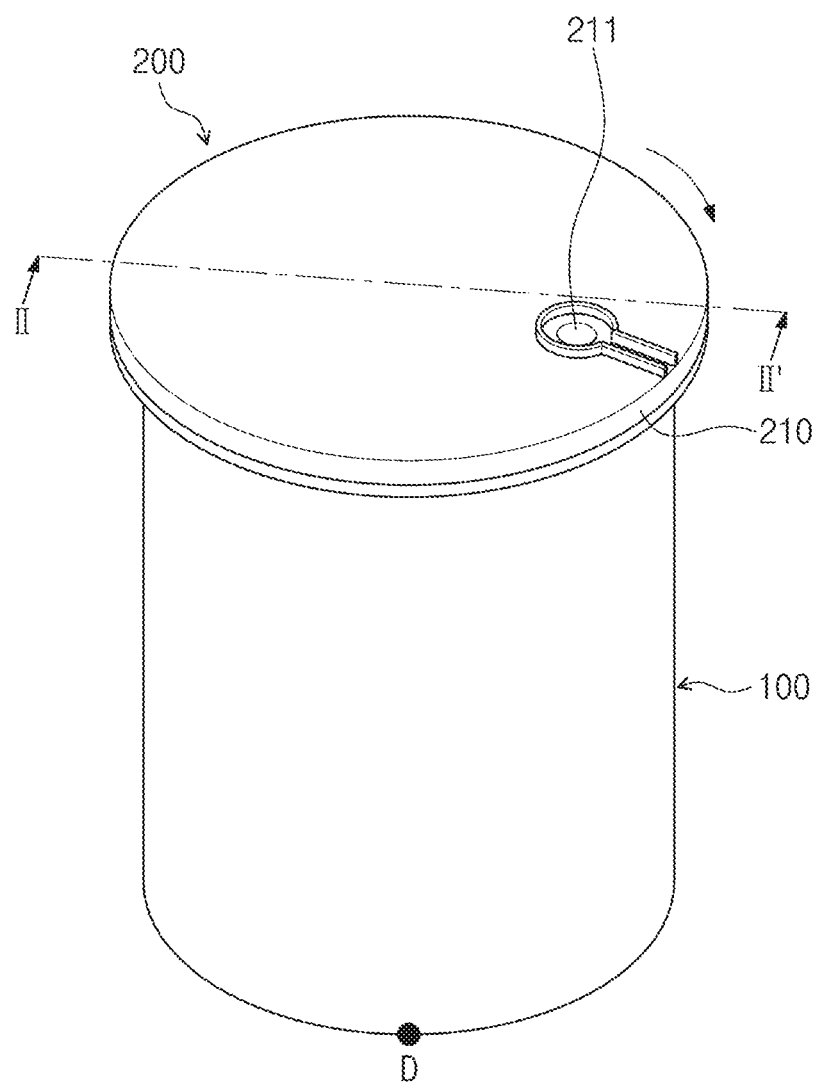
Figure 8B:
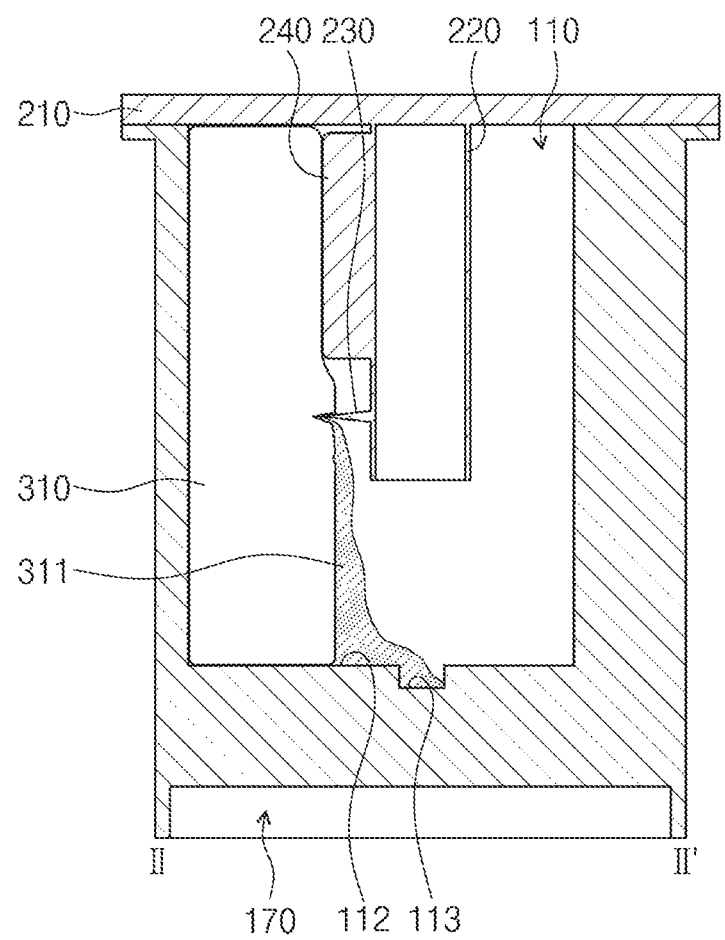
FIG. 8B is a cross-sectional view taken along line II-II' of FIG. 8A.

Referring to FIGS. 8A and 8B, the head unit 200 may rotate clockwise so that the cutting portion 230 and the pressing portion 240 of the head unit 200 contact the first container 310. Referring to FIGS. 7A, 8A, 9A, 10A, and 11A, a point D is marked on the main body 100 to check a rotation angle of the head unit 200. Since the minimum distance between the first container 310 and the pillar 220 is less than that between the side surface 111 of the main groove 110 and the pillar 220, the cutting portion 230 and the pressing portion 240 may contact the first container 310 according to the rotation of the head unit 200. As the cutting portion 230 contacts, the first container 310 may be cut. As the first container 310 is cut, the first solution 311 in the first container 310 may be discharged. As the pressing portion contacts, the first container 310 may be pressed. As the first container 310 is pressed by the pressing portion 240, the first solution 311 in the first container 310 may be relatively smoothly discharged. The first solution 311 discharged from the first container 310 may be supplied to the insertion groove 120 along the first bottom surface 112 and the second bottom surface 113 of the main groove 110. The first solution 311 supplied to the insertion groove 120 may dissolve the body tissue BT in the insertion groove 120. The body tissue BT may be completely dissolved by the first solution 311 in the insertion groove 120. The dissolving of the body tissue BT by the first solution 311 may include heating the first solution 311 by the heater 180 of the main body 100. As the first solution 311 is heated by the heater 180, a dissolution rate of the body tissue BT may increase. The dissolving of the body tissue BT by the first solution 311 may be performed within one day.

Unlike as illustrated, a hot wire covering the main body 100 may be provided instead of the heater 180, and the first solution 311 may be heated by the hot wire.

When the first container 310 is made of glass, the first container 310 may be crushed by the pressing portion 240, and the first solution 311 in the first container 310 may be supplied to the insertion groove 120.

Figure 9A:
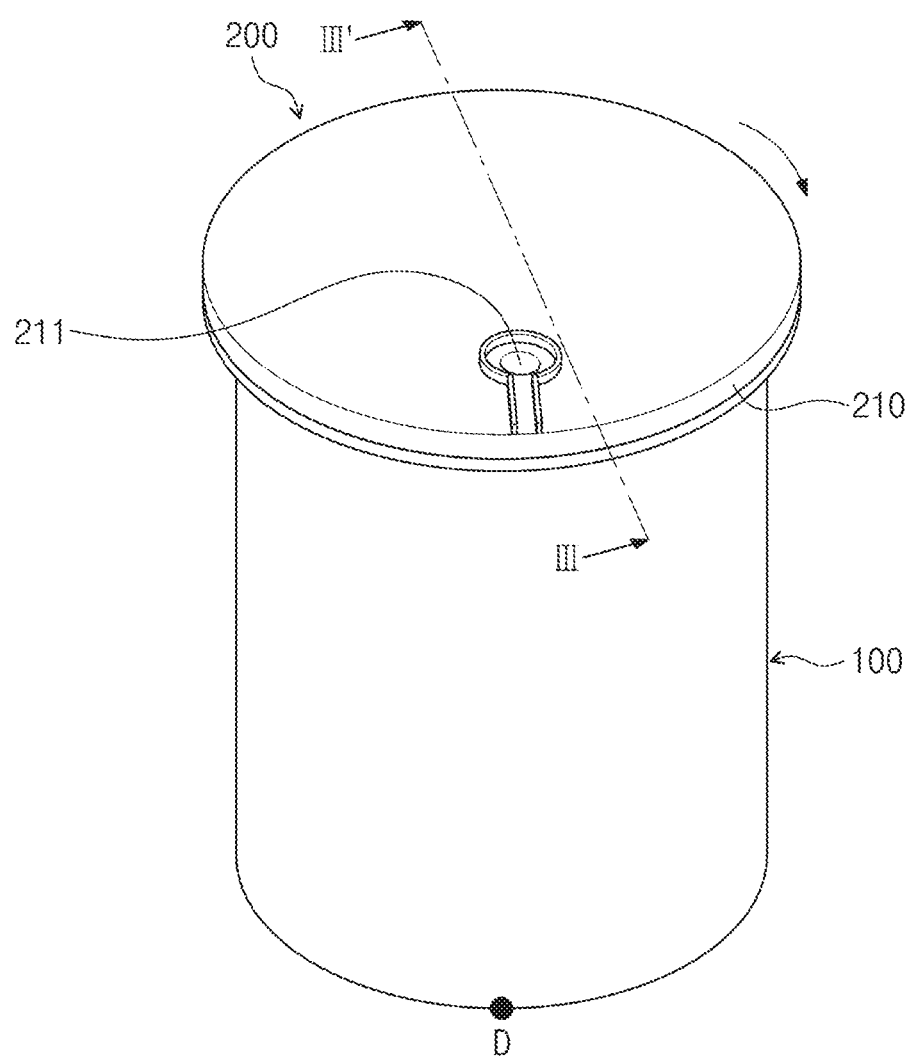
Figure 9B:
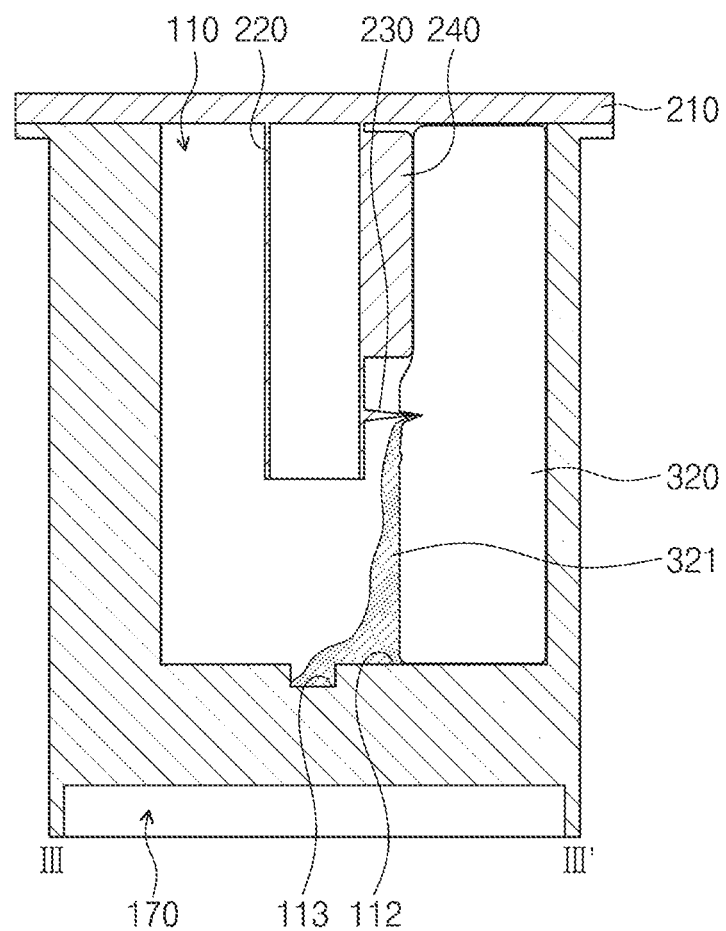
FIG. 9B is a cross-sectional view taken along line III-III' of FIG. 9A.

Referring to FIGS. 9A and 9B, the head unit 200 may rotate clockwise so that the cutting portion 230 and the pressing portion 240 of the head unit 200 contact the second container 320. Since the minimum distance between the second container 320 and the pillar 220 is less than that between the side surface 111 of the main groove 110 and the pillar 220, the cutting portion 230 and the pressing portion 240 may contact the second container 320 according to the rotation of the head unit 200. As the cutting portion 230 contacts, the second container 320 may be cut. As the second container 320 is cut, the second solution 321 in the second container 320 may be discharged. As the pressing portion 240 contacts, the second container 320 may be pressed. As the second container 320 is pressed by the pressing portion 240, the second solution 321 in the second container 320 may be relatively smoothly discharged. The second solution 321 discharged from the second container 320 may be supplied to the insertion groove 120 along the first bottom surface 112 and the second bottom surface 113 of the main groove 110. The second solution 321 supplied to the insertion groove 120 may be mixed with the first solution 311. As the first solution 311 is mixed with the second solution 321, the acidity (pH) of the first solution 311 may increase. The first solution 311 may be primarily neutralized by the second solution 321. As the first solution 311 and the second solution 321 are mixed with each other, a biological material BM may be produced.

When the second container 320 is made of glass, the second container 320 may be crushed by the pressing portion 240, and the second solution 321 in the second container 320 may be supplied to the insertion groove 120.

Figure 10A:
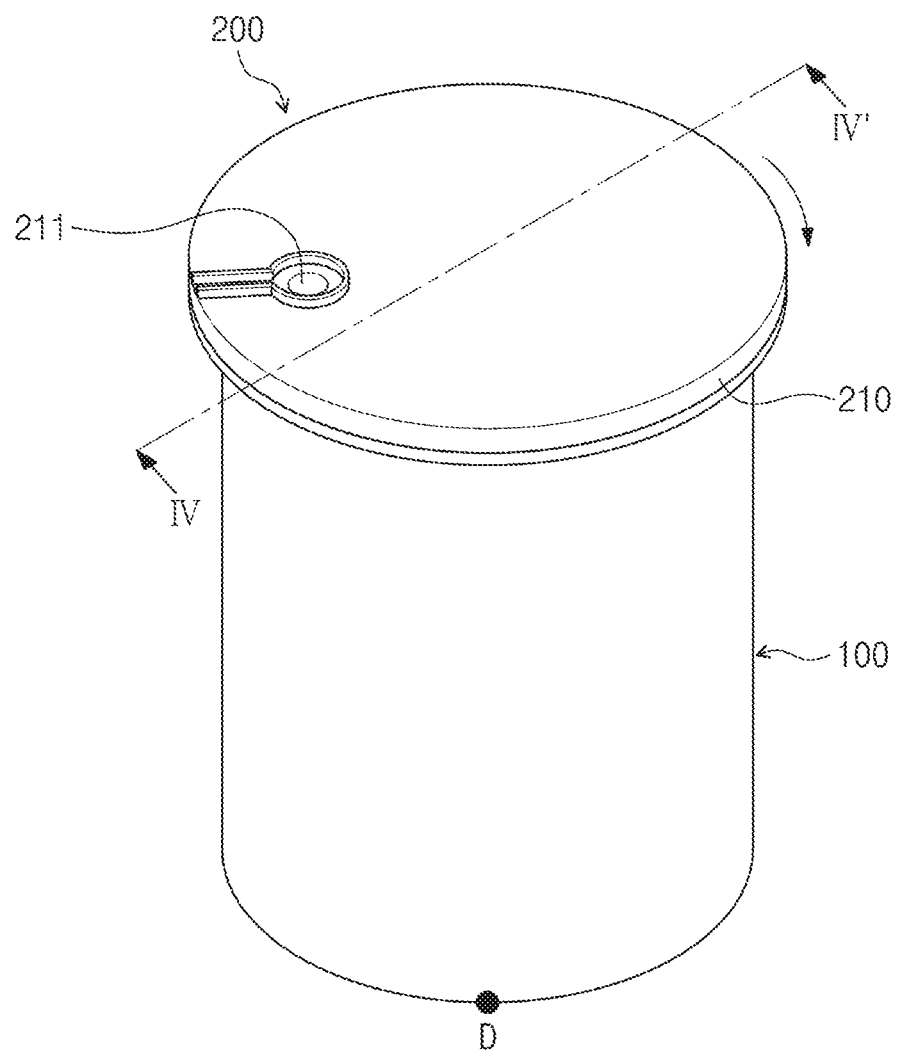
Figure 10B:
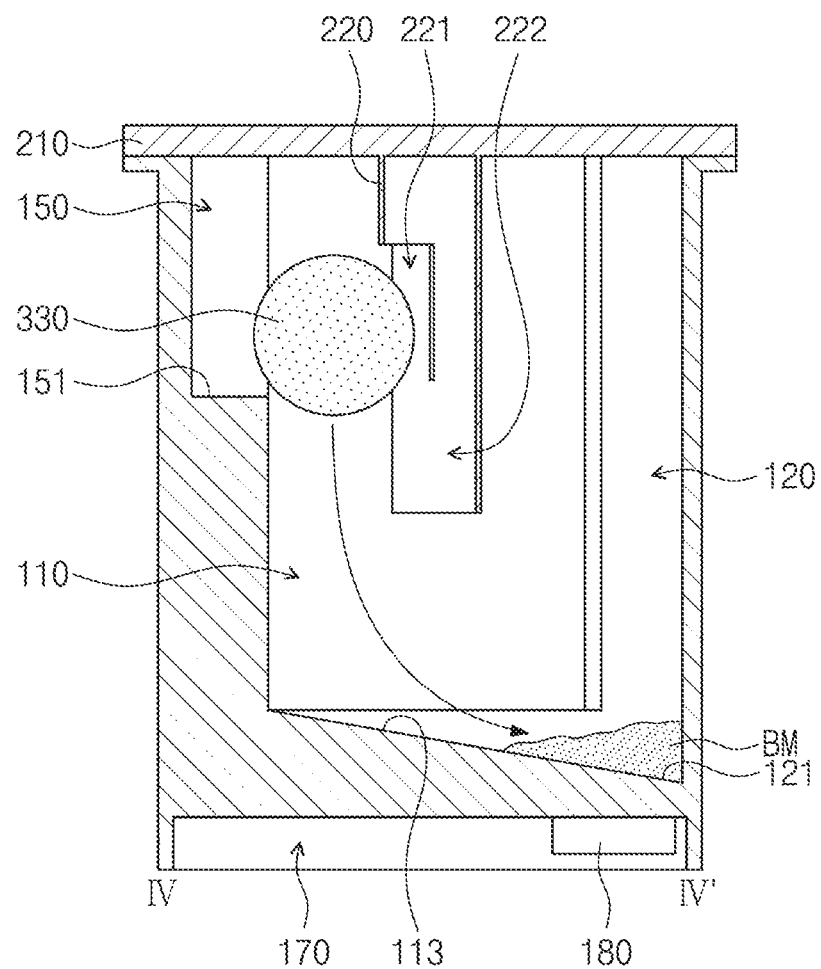
FIG. 10B is a cross-sectional view taken along line IV-IV' of FIG. 10A.

Referring to FIGS. 10A and 10B, the head unit 200 may rotate clockwise so that the first and second recesses 221 and 222 of the pillar 220 face the neutralizer groove 150 of the main body 100. As the neutralizer groove 150 faces the first recess 221, the first neutralizer 330 supported by the pillar 220 may enter in the first recess 221. As entered in the first recess 221, the first neutralizer 330 may be fallen from the neutralizer groove 150 to the main groove 110. The first neutralizer 330 may be fallen to the second bottom surface 113 of the main groove 110. The first neutralizer 330 fallen to the second bottom surface 113 of the main groove 110 may move to the insertion groove 120 along the second bottom surface 113. The first neutralizer 330 moved to the insertion groove 120 may react with the biological material BM to increase an acidity (pH) of the biological material BM. The biological material BM may be secondarily neutralized by the first neutralizer 330.

Figure 11A:
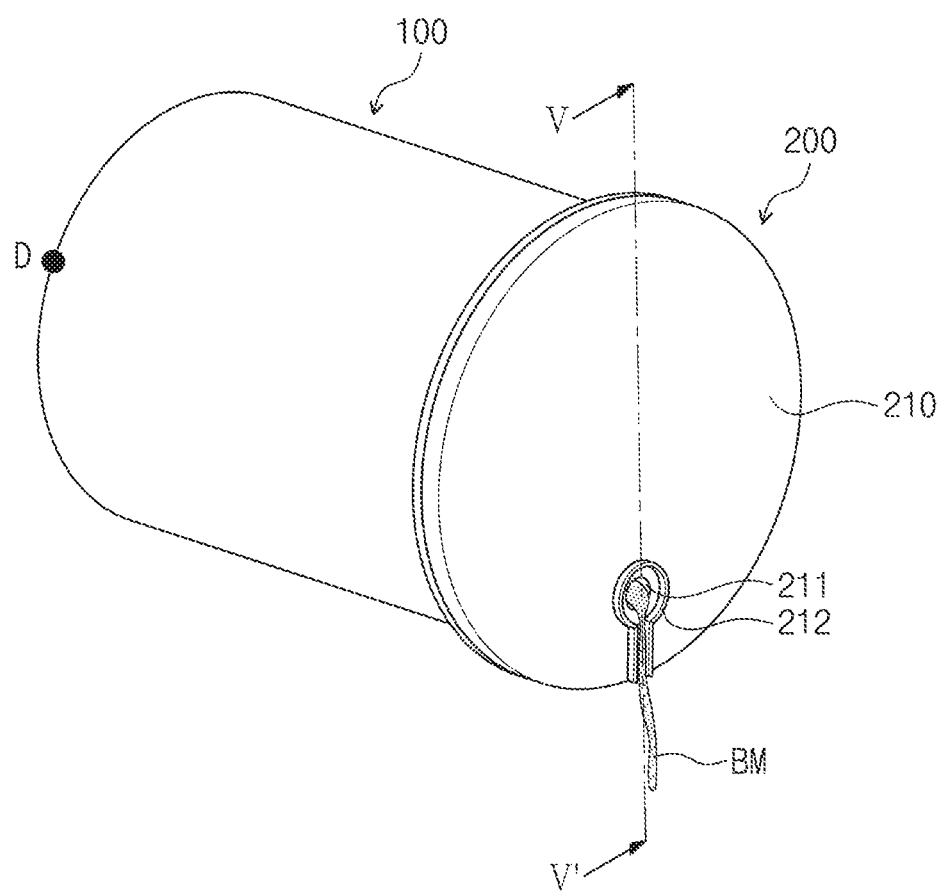
Figure 11B:
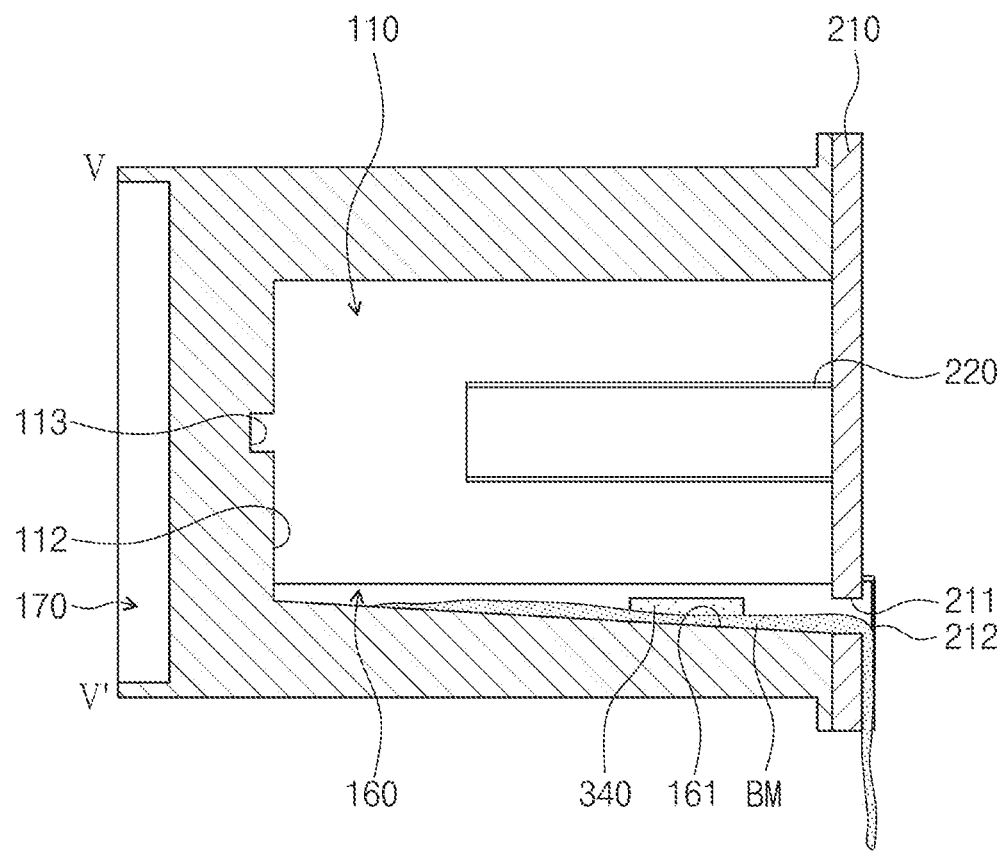
FIG. 11B is a cross-sectional view taken along line V-V' of FIG. 11A.

Referring to FIGS. 11A and 11B, the head unit 200 may rotate counter-clockwise so that the base opening 211 of the base 210 of the head unit 200 perpendicularly overlaps the discharge groove 160. The biological material BM in the insertion groove 120 of the main body 100 may be discharged to the base opening 211 by allowing the main body 100 to be inclined. The biological material BM may move along the discharge surface 161 of the discharge groove 160 and be discharged to the base opening 211. While moving along the discharge surface 161 of the discharge groove 160, the biological material BM may react with the second neutralizer 340 attached to the discharge surface 161. The acidity (pH) of the biological material BM may increase by reacting with the second neutralizer 340. The biological material BM may be tertiarily neutralized by the second neutralizer 340. The acidity (pH) of the biological material BM discharged to the base opening 211 may be neutral.

The biological material BM discharged to the base opening 211 may move to an edge of the base 210 by the barrier 212 and be fallen from the head unit 200. A product using the biological material BM may be made by collecting the biological material BM fallen from the head unit 200.

In the embodiment, the first solution 311 for dissolving the body tissue BT may be acidic. In the embodiment, by using the second solution 321, the first neutralizer 330, and the second neutralizer 340, the finally discharged biological material BM may be neutral, and security of the biological material may be secured.

In the embodiment, the biological material BM may be manufactured according to the inserting of the body tissue BT and the rotating of the head unit 200. As described above, the biological material manufacturing device according to an embodiment of the inventive concept may simply manufacture the biological material BM.

The biological material manufacturing device according to the embodiment of the inventive concept may manufacture a biological material having a neutral acidity and secure stability of the biological material.

Although the exemplary embodiments of the present invention have been described, it is understood that the present invention should not be limited to these exemplary embodiments but various changes and modifications can be made by one ordinary skilled in the art within the spirit and scope of the present invention as hereinafter claimed. Therefore, the preferred embodiments should be considered in descriptive sense only and not for purposes of limitation, and also the technical scope of the invention is not limited to the embodiments.

What is claimed is:

1. A biological material manufacturing device comprising:
   a main body; and
   a head unit that is rotatable on the main body,
   wherein the main body comprises a main groove and a first container groove connected to the main groove,
   the head unit comprises a pillar provided in the main groove and a protruding part that protrudes from the pillar,
   a first container, in which a first solution is accommodated, is provided in the first container groove,
   the first solution is an acidic solution, and
   the protruding part cuts or crushes the first container according to rotation of the head unit.

2. The biological material manufacturing device of claim 1, wherein the main body further comprises a second container groove connected to the main groove,
   a second container, in which a second solution is accommodated, is provided in the second container groove, and
   the second solution reacts with the first solution to neutralize the first solution.

3. The biological material manufacturing device of claim 1, wherein the main body further comprises an insertion groove connected to the main groove,
   each of a bottom surface of the main groove and a bottom surface of the insertion groove is inclined to a top surface of the main body, and
   the bottom surface of the insertion groove has a level less than that of the bottom surface of the main groove.

4. The biological material manufacturing device of claim 3, wherein the main body further comprises a heater disposed below the insertion groove.

5. The biological material manufacturing device of claim 1, wherein the main body further comprises a neutralizer groove connected to the main groove,
   a first neutralizer supported by the pillar is provided in the neutralizer groove,
   the pillar comprises a recess at a side surface thereof, and
   the first neutralizer enters into the recess according to the rotation of the head unit to neutralize the first solution.

6. The biological material manufacturing device of claim 1, wherein the main body further comprises a discharge groove connected to the main groove,
   the discharge groove comprises a discharge surface that is inclined to a top surface of the main body,
   the discharge groove further comprises a second neutralizer disposed on the discharge surface, and
   the second neutralizer neutralizes the first solution.

7. A method for driving a biological material manufacturing device, comprising:
   providing the biological material manufacturing device of claim 1;
   inserting a body tissue into the main body;
   dissolving the body tissue in the first solution; and
   neutralizing the first solution,
   wherein the dissolving of the body tissue in the first solution comprises:
   disposing the first container, in which the first solution is accommodated, in the first container groove of the main body;

rotating the head unit disposed on the main body; and
cutting or crushing the first container by the protruding part of the head unit.

8. The method of claim 7, wherein the neutralizing of the first solution comprises:
disposing a second container, in which a second solution is accommodated, in a second container groove of the main body;
rotating the head unit; and
cutting or crushing the second container by the protruding part of the head unit.

9. The method of claim 7, wherein the neutralizing of the first solution comprises:
producing a biological material that is primarily neutralized by mixing the first solution with a second solution;
secondarily neutralizing the primarily neutralized biological material by being reacted with a first neutralizer; and
tertiarily neutralizing the secondarily neutralized biological material by being reacted with a second neutralizer.

* * * * *